United States Patent
Fuchs (10) Patent No.: US 9,700,208 B2
(45) Date of Patent: Jul. 11, 2017

(54) SYSTEMS AND METHODS FOR HYBRID RADIO COMMUNICATION FOR MEDICAL TELEMETRY

(71) Applicant: Mindray DS USA, Inc., Mahwah, NJ (US)

(72) Inventor: Kenneth J. Fuchs, Wayland, MA (US)

(73) Assignee: SHENZHEN MINDRAY BIO-MEDICAL ELECTRONICS CO. LTD., Shenzhen (CN)

(*) Notice: Subject to any disclaimer, the term of this patent is extended or adjusted under 35 U.S.C. 154(b) by 101 days.

(21) Appl. No.: 14/255,809

(22) Filed: Apr. 17, 2014

(65) Prior Publication Data

US 2015/0297081 A1    Oct. 22, 2015

(51) Int. Cl.
| | |
|---|---|
| *G08C 19/22* | (2006.01) |
| *H04Q 9/00* | (2006.01) |
| *A61B 5/00* | (2006.01) |
| *H04W 40/02* | (2009.01) |
| *G06F 19/00* | (2011.01) |

(52) U.S. Cl.
CPC ........ *A61B 5/0015* (2013.01); *G06F 19/3418* (2013.01); *H04W 40/02* (2013.01)

(58) Field of Classification Search
CPC .......... H04Q 9/00; H04Q 9/14; A61B 5/0002; G08C 17/02
USPC ................ 340/870.1, 870.7, 870.8; 343/779; 116/124.1
See application file for complete search history.

(56) References Cited

U.S. PATENT DOCUMENTS

| | | | | |
|---|---|---|---|---|
| 5,675,582 | A * | 10/1997 | Hummel | H04Q 3/66 370/255 |
| 2002/0095271 | A1* | 7/2002 | Brinsfield | H04B 1/406 702/189 |
| 2004/0131125 | A1* | 7/2004 | Sanderford, Jr. | H04L 5/06 375/261 |
| 2005/0047379 | A1* | 3/2005 | Boyden | H04B 1/7163 370/338 |
| 2006/0206011 | A1* | 9/2006 | Higgins | G06F 19/3418 600/300 |
| 2009/0135838 | A1* | 5/2009 | Rouyer | H04L 12/4625 370/401 |

FOREIGN PATENT DOCUMENTS

EP    1113583 A2 *   7/2001   ............. H04B 1/005

* cited by examiner

*Primary Examiner* — George Bugg
*Assistant Examiner* — Anthony D Afrifa-Kyei
(74) *Attorney, Agent, or Firm* — Kory D. Christensen; Polsinelli LLP (57) ABSTRACT

A portable telemetry device includes a measurement component, a unidirectional radio, a bidirectional radio, and a communication component. The measurement component is configured to receive, from at least one sensor, physiological data representative of a physiological condition of a patient. The unidirectional radio is configured to transmit signals in a first wireless frequency band. The bidirectional radio is configured to transmit and receive signals in a second wireless frequency band different from the first wireless frequency band. The communication component is configured to transmit the physiological data using the unidirectional radio and transmit and receive control data using the bidirectional radio.

30 Claims, 4 Drawing Sheets

SYSTEMS AND METHODS FOR HYBRID RADIO COMMUNICATION FOR MEDICAL TELEMETRY

TECHNICAL FIELD

The present disclosure relates to medical monitoring and more particularly relates to systems, methods, and devices for hybrid radio communication for medical telemetry.

DETAILED DESCRIPTION OF PREFERRED EMBODIMENTS

Modern technology practice makes extensive use of electronic monitoring of vital signs and other physiological parameters of patients. In some cases, remote monitoring of physiological parameters, or telemetry, is used to allow nurses, doctors, and/or computing devices to determine the health of a patient or detect problems with the patient when the nurse or doctor is not present with the patient. In some cases, wireless telemetry devices worn by a patient may allow the patient to move around and/or be easily moved between locations while maintaining monitoring of the patient's vital signs.

One example of a portable telemetry device is the Mindray Telepack® which uses proprietary one-way radios (transmit only) operating in very-high frequency (VHF) or ultra-high frequency (UHF) wireless bands to stream patient data over an antenna system to a receiver. In the United States, the wireless medical telemetry service (WMTS) provides dedicated protected bands which have been allocated for this purpose and which many hospitals prefer to use over the more widely used industrial, scientific, and medical (ISM) radio bands. Currently the WMTS provides licensed bands in a 608 to 614 megahertz (MHz) range (also known as the 608 MHz band), a 1395 to 1400 MHz range (also known as the 1400 MHz band), and a 1427 to 1432 MHz range. The ISM bands include the popular 2.4 gigahertz (GHz) range (which currently includes frequencies from 2.4 to 2.5 GHz) range and a 5 GHZ range (which currently includes frequencies from 5.725 to 5.875 GHz) which may be used by routers, wireless home telephones, or the like. Additionally, the Federal Communication Commission (FCC) in the United States is contemplating other potential bands such as a 3 GHz band for medical applications and a 2.3 GHz band for medical body area networks (MBANs). Other frequencies and frequency bands are set aside for use by specific companies or providers, such as cellular phone service providers. For example, wireless service providers may use licensed spectrums for communication with smartphones, tablets, wireless hotspots, or other mobile communication devices.

Note that the designation of frequencies or frequency bands for a specific purpose, whether licensed or unlicensed, may be under the control of a governmental body or standard setting organization. Thus, frequencies and frequency bands set aside for various purposes are subject to change over time and also can vary between different countries or geographic regions. For example, the FCC may eliminate, add, narrow, broaden, or create new licensed or designated bands. Furthermore, different countries may set aside different frequencies or frequency bands for medical, cellular, industrial, or other services. Although the present disclosure generally discusses embodiments in relation to licensed and/or designated frequencies within the United States, the present disclosure also contemplates and encompasses embodiments having modifications or variations for other countries or changes to designated frequency bands within a country.

Currently, hospitals and other medical providers often use the WMTS bands over the ISM bands because they require less active management and present a smaller patient safety risk. For example, because there is arguably less chance of interference in the licensed frequencies, there is a reduced likelihood that a patient's signals will be lost or not received and that a nurse, doctor, or monitoring system will fail to detect problems with the patient. As used herein the terms "protected" and "licensed" radio bands are given to mean that use of wireless carrier wave frequencies within a specific range are set aside for a specific purpose, industry, or entities and/or cannot be used without registering usage with a regulating body.

Some telemetry devices may use the same protected WMTS bands but have bidirectional radios which allow the device to have additional functionality and act more like a stand-alone patient monitor because they are able to receive, as well as send, data. Unfortunately, off-the-shelf commercially available radios are generally not available for the protected WMTS bands, and designing proprietary solutions for these bidirectional radios is quite complex and expensive. For example, since the quantities for these radios that operate on protected frequencies are relatively small, the radios and access points are expensive to produce. Furthermore, significant costs for developing new communication protocols are also required. Even with these efforts to develop bidirectional radios, resulting data rates are still very low and power consumption is increased when compared with a unidirectional radio or off-the-shelf radios for ISM bands.

To overcome the expense, low data rates, and high energy usage while still allowing for bidirectional communication, the present disclosure proposes that patient-worn telemetry devices use hybrid radio systems, methods, and devices. According to one embodiment, a patient worn telemetry device or other portable telemetry device includes a measurement component, a unidirectional radio, a bidirectional radio, and a communication component. The measurement component is configured to receive, from at least one sensor, physiological data representative of a physiological condition of a patient. The unidirectional radio is configured to transmit signals in a first wireless frequency band and the bidirectional radio is configured to transmit and receive signals in a second wireless frequency band that does not overlap with the first wireless frequency band. The communication component is configured to transmit the physiological data using the unidirectional radio and transmit and receive control data using the bidirectional radio.

For example, the unidirectional radio may include a VHF/UHF radio in a protected radio band while the bidirectional radio may include an off-the-shelf radio such as a radio that implements an institute for electrical and electronics engineers (IEEE) 802.11 standard (known to industry groups as Wi-Fi), such as an 802.11 a, b, g, or n radio standard. In one embodiment, the bidirectional radio may include a radio that operates within a licensed cellular spectrum. For example, the bidirectional radio may implement a 3G, LTE, or any other wireless communication standard. The unidirectional radio may be used to achieve a low technology and low patient risk for communication of continuous or frequent patient information such as physiological waveforms, measured parameters, and/or alarm information. Use of a unidirectional radio that operates in a protected band will provide the dependability that medical teams need for life-critical information. The off-the-shelf radio will be used to listen and respond to commands to the device. For example, these commands may be included in control data to configure operation of the portable telemetry device such as by setting alarm limits, resetting alarms, transferring stored data, etc.

With regard to energy usage, the unidirectional radio will consume less power than a bidirectional radio, especially for radios in a protected band. Also, the duty cycle for the bidirectional radio may be reduced or very low since many control activities may be very infrequently used. For example, the bidirectional radio may only be required to receive and/or transmit data a few times per hour so the power consumption for this radio should be minimal. In one embodiment, because there are two radios, the portable telemetry device may provide a backup feature where the bidirectional radio can take over for the unidirectional radio if the patient moves outside of a range for the unidirectional radio but is still in range for the bidirectional radio.

The use of a bidirectional radio and unidirectional radio may provide a plurality of benefits and advantages. For example, design complexity is reduced because unidirectional systems are much simpler and bidirectional communication is provided using common off-the-shelf parts. Furthermore, high-speed off-the-shelf radios could be used for some features that require high-speed communications. As discussed above, if the unidirectional radio fails, the bidirectional radio can be activated as a backup. This backup feature provides for improved patient safety. In addition, the use of two radios and the ability to route physiological data over the bidirectional radio may allow a patient to roam out of conventional monitoring ranges. For example, some parts of a hospital may provide Wi-Fi coverage without providing coverage for a licensed unidirectional radio. As another example, cellular coverage may be available within the hospital or regions of the hospital as well as a surrounding region. Furthermore, the same portable telemetry device may be used for in-hospital, in-ambulance, and/or in-home scenarios where coverage for WMTS frequencies are not available. For example, medical personnel may not need to switch telemetry devices and/or sensors as they transition from a home or an ambulance, where coverage for WMTS protected bands may not be available, to a hospital, where coverage for the WMTS protected bands may be available and preferred. As another example, the same portable telemetry device may be capable of connecting to Wi-Fi networks, cellular networks, and/or hospital WMTS networks. Thus, increased coverage may be available to allow for reduced effort in transporting a patient and/or increasing reliability of monitoring the patient.

In a further embodiment, a portable telemetry device may include a first bidirectional radio and a second bidirectional radio, without any unidirectional radio. The first bidirectional radio may include a radio that operates within a protected or unprotected frequency band. For example, the first bidirectional radio may operate in a ISM or WMTS frequency. The second bidirectional radio may include a cellular radio for communicating in a cellular network. The first and second bidirectional radios may provide a large coverage area so that a patient can be monitored at a hospital location and/or a variety of non-hospital locations, such as within an ambulance or a home of a patient. In one embodiment, the portable telemetry device may include two bidirectional radios and a unidirectional radio. For example, the unidirectional radio may operate within a protected WMTS band, the first bidirectional radio may operate within an ISM band (such as a Wi-Fi frequency), and the second bidirectional radio may operate within a licensed band corresponding to a cellular network.

A detailed description of systems and methods consistent with embodiments of the present disclosure is provided below. While several embodiments are described, it should be understood that disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Figure 1:
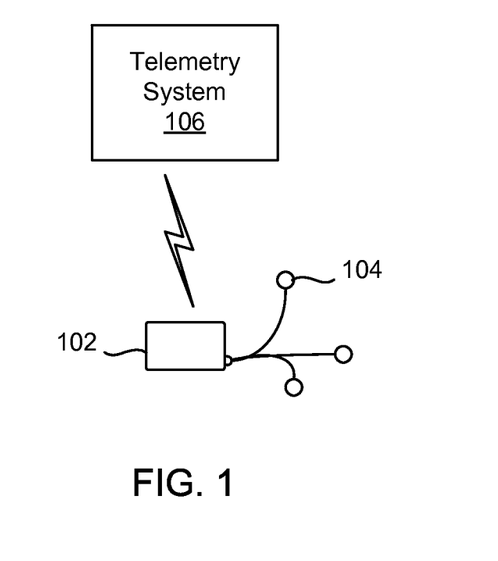
FIG. 1 is a schematic block diagram illustrating a portable telemetry device in communication with a telemetry system, according to one embodiment.

Turning to the figures, FIG. 1 is a schematic diagram illustrating a telemetry system 106 and a portable telemetry device 102 for medical telemetry. In one embodiment, the portable telemetry device 102 includes a telemetry device worn by a patient. For example, the patient may be free to walk or move while wearing the portable telemetry device 102 due to size and capability for wireless communication.

The portable telemetry device 102 may include a portable device comprising a housing containing a processor, circuitry, computer readable memory, antenna, radios, and/or the like. The portable telemetry device 102 may have a size such that it can be worn by a patient while allowing the patient to move freely. The telemetry device 102 may include one or more ports for coupling to sensors and receiving signals from the sensors. The portable telemetry device 102 may include a human-machine interface, which may include a display, one or more buttons, and/or indicator lights to allow a human to determine a status of the portable telemetry device 102, enter information, or otherwise interact with the portable telemetry device 102.

The portable telemetry device 102 is in wireless communication with the telemetry system 106. Connected to the telemetry device 102 are a plurality of sensors 104 which may be used to measure patient parameters and/or obtain patient waveforms. For example, the sensors 104 may include one or more electrocardiography (ECG) sensors, a pulse oximetry sensor (e.g., $SpO_2$), and/or any other sensors. The portable telemetry device 102 may receive signals from the sensors 104 as analog or digital data signals indicating a physiological condition of a patient. The portable telemetry device 102 may transmit physiological data to the telemetry system 106 using a unidirectional radio. For example, the telemetry device 102 may forward processed or unprocessed sensor data to the telemetry system 106 so that a doctor, nurse, or other medical personnel can monitor a condition of the patient.

In one embodiment, the portable telemetry device 102 may transmit the physiological data as numerical and/or waveform data using a protected frequency using a unidirectional radio. The data may be sent at defined intervals or may be sent every time a buffer is filled with new patient data. In one embodiment, the portable telemetry device 102 may also send an identifier which identifies the patient or portable telemetry device 102 to which the physiological data corresponds. The portable telemetry device 102 may also include a bidirectional radio that can be used for bidirectional communication with the telemetry system 106 to receive and/or send control data.

The telemetry system 106 may include a computing device such as a computer, server, or the like. The telemetry system 106 may include a processor, circuitry, computer readable memory, antenna, radios, communication ports, and/or the like. In one embodiment, the telemetry system 106 includes a computing system for a central nursing station. For example, the telemetry system 106 may include a computing system for an intensive care ward, step down ward, or in-patient ward.

The telemetry system 106 receives the physiological data from the portable telemetry device 102 and stores and/or processes the physiological data. In one embodiment, the telemetry system 106 stores the physiological data in memory for later access and/or analysis. In one embodiment, the telemetry system 106 processes the physiological data to detect problems for the patient, detect whether there is an alarm condition, or perform other analysis. For example, the telemetry system 106 may report an alarm condition to a nurse, doctor, or other medical personnel.

The telemetry system 106 may also provide control data to the portable telemetry device 102 to configure alarm settings, reset alarms, determine a state or location of the portable telemetry device 102, transfer stored data, or otherwise configure operation of the portable telemetry device 102. In one embodiment, the telemetry system 106 may send and receive control data between the portable telemetry device 102 to determine that messages were received or that instructions corresponding to control data were performed.

Figure 2:
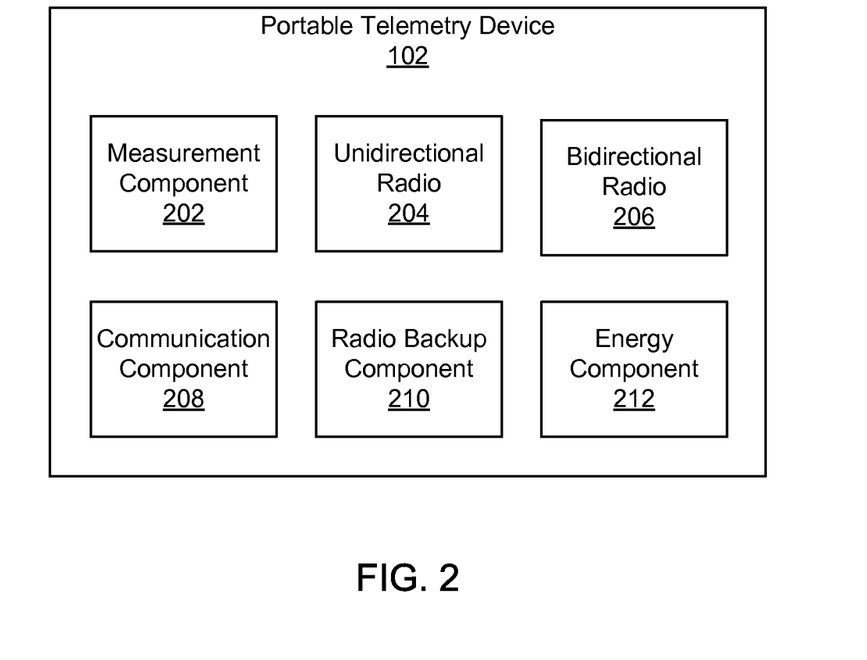
FIG. 2 is a schematic block diagram illustrating a portable telemetry device, according to one embodiment.

FIG. 2 is a schematic block diagram illustrating components of a portable telemetry device 102, according to one embodiment. The portable telemetry device 102 is shown with a measurement component 202, a unidirectional radio 204, a bidirectional radio 206, a communication component 208, a radio backup component 210, and an energy component 212. The components 202-212 are given by way of example only and may not all be included in all embodiments. In one embodiment, the portable telemetry device 102 may be used for patient monitoring within a hospital, ambulance, home, or other environment.

The measurement component 202 receives physiological data from one or more sensors. The measurement component 202 may include a port where a sensor, cable, or one or more leads of a sensor can be coupled to the portable telemetry device 102. The measurement component 202 may receive the physiological data in analog, digital, or other format. In one embodiment, the measurement component 202 receives the physiological data in an analog format and converts the data to a digital format for communication to a telemetry system 106.

The unidirectional radio 204 and bidirectional radio 206 are configured to communicate with a telemetry system 106 in different frequencies or frequency bands. The unidirectional radio 204 includes a transmitter but omits a receiver or receiver circuitry. The omission of a receiver and/or receiver circuitry for the unidirectional radio 204 simplifies the radio and may reduce costs, energy usage, or the like. In one embodiment, the unidirectional radio 204 includes an inactive receiver or receiver circuitry. In one embodiment, the unidirectional radio 204 includes an antenna and circuitry configured to transmit signals in a VHF or UHF frequency. The unidirectional radio 204 may be configured to transmit signals at a licensed or protected frequency, such as within a frequency band defined by the WMTS. Example frequency bands within which the unidirectional radio 204 may transmit signals include a 608 to 614 MHz frequency band, a 1395 to 1400 MHz frequency band, and a 1427 to 1432 MHz frequency band. Because the unidirectional radio 204 is only configured to transmit signals, the portable telemetry device 102 may be incapable of receiving signals within a frequency band in which the unidirectional radio 204 is configured to transmit signals.

In one embodiment, the unidirectional radio 204 may be used to transmit time sensitive or critical data to the telemetry system. For example, the unidirectional radio 204 may operate in a frequency range that is licensed and thus may be better managed and less likely to experience harmful interference. In one embodiment, the time-sensitive or critical data may include the physiological data that is representative of a current physiological condition of an attached patient. The physiological data may include data regarding cardiac health, respirations, oxygen levels, or data regarding any other physiological condition of a patient. Alternatively or additionally, the time sensitive or critical data may include identification information and/or an alarm signal. The identification information may include a patient identifier number that corresponds to the patient at check-in or may be any other identifier used to identify patients. The alarm signal may include a signal that is transmitted when an alarm condition is met. Example alarm conditions may include high or low heart rates, high or low breathing rates, high or low oxygen levels, or any other physiological condition. Other alarm conditions are also possible regarding a state of the portable telemetry device 102. The signals transmitted by the unidirectional radio 204 may be received by a receiver of the telemetry system 106 for storage, monitoring, processing, or other usage.

The bidirectional radio 206 is configured to both transmit and receive signals within a corresponding wireless frequency band. In one embodiment, the unidirectional radio 204 and the bidirectional radio 206 may be configured to operate within non-overlapping frequency bands. For example, the unidirectional radio 204 may operate within a licensed wireless spectrum while the bidirectional radio 206 operates within an unlicensed wireless spectrum. In one embodiment, the bidirectional radio 206 may operate within an unlicensed ISM band such as a 2.4 to 2.5 GHz range and a 5.725 to 5.875 GHz range. The bidirectional radio 206 may include an off-the-shelf radio such as an 802.11 radio.

The bidirectional radio 206 is capable of bidirectional communication (reception and transmission) with the telemetry system 106. In one embodiment, the bidirectional radio 206 may be used for a control channel or for control data between the portable telemetry device 102 and the telemetry system 106. For example, the bidirectional radio 206 may be used to receive control data to configure operation of the portable telemetry device 102 and/or acknowledge to a telemetry system 106 that a signal was received or an instruction performed. Examples of control data that may be sent between the portable telemetry device 102 and the telemetry system 106 include alarm limit data, alarm reset data, configuration data for the portable telemetry device 102, and stored patient data as well as acknowledgement signals or the like.

The communication component 208 controls operation of the radios 204, 206 and what data is sent over which radio. For example, the communication component 208 may transmit the physiological data using the unidirectional radio 204 and transmit and receive control data using the bidirectional radio 206. In one embodiment, the communication component 208 transmits time-sensitive data over the unidirectional radio 204. The time-sensitive data may include data that is critical for monitoring a patient such as the physiological data received from sensors, patient identification information, and/or an alarm signal. In one embodiment, the communication component 208 transmits non-critical or non-time-sensitive data over the bidirectional radio 206. Example data to be transmitted and/or received using the bidirectional radio 206 may include control data that configures operation of the portable telemetry device 102 or the telemetry system 106. For example, the communication component 208 may use the bidirectional radio 206 to send or receive one or more of alarm limit data, alarm reset data, configuration data for the portable telemetry device 102, and stored patient data. The alarm limit data may include data that defines limits, which when exceeded or fallen below, will trigger an alarm. The portable telemetry device 102 may configure alarm settings based on the alarm limit data. The alarm reset data may include data that indicates that an alarm should be reset. For example, after an alarm is triggered, a nurse or other medical personnel may check on the patient. The nurse may cause an alarm reset signal to be sent to indicate that an issue is being addressed or that an issue has been resolved. The configuration data may indicate what physiological data to report, how frequently it should be reported, or the like. In one embodiment, the configuration data may include a battery level of the portable telemetry device 102 or otherwise indicate whether the portable telemetry device 102 is operating correctly.

The radio backup component 210 is configured to route physiological data or time-sensitive data over the bidirectional radio 206 when the unidirectional radio 204 is out of range and the bidirectional radio is still in range. For example, the telemetry system 106 may indicate, using control data, that the unidirectional radio 204 of the portable telemetry device 106 is out of range and instructs the portable telemetry device 102 to begin sending physiological data, or other data types previously transmitted using the unidirectional radio 204, over the bidirectional radio 206.

The energy component 212 may help reduce energy usage of the portable telemetry device 102 by reducing energy consumption of the bidirectional radio 206. In one embodiment, the energy component 212 reduces a duty cycle of a bidirectional radio 206 to reduce energy consumption. In one embodiment, the energy component 212 includes a clock with a variable cycle rates or two or more clocks with different cycle rates which can be used to affect the duty cycle of the portable telemetry device 102. In one embodiment, the bidirectional radio 206 may include a radio that is capable of handling high data rates but also consumes more energy when the high data rates are used. The energy component 212 may place the bidirectional radio 206 in a low power state or low duty cycle state such that bidirectional communication may be maintained but reduces the amount of energy needed to operate the bidirectional radio 206. In some embodiments, the bidirectional radio 206 may only be required to communicate or receive control data at very low data rates or very low duty cycles. However, if the radio backup component 210 causes the bidirectional radio 206 to take over for the unidirectional radio 204, the increased capability may be desirable. The energy component 212 may dynamically increase or reduce the duty cycle based on whether physiological, or other potentially time-critical data, is being transmitted or received using the bidirectional radio 206. In one embodiment, the energy component 212 defaults to causing the bidirectional radio 206 to operate at a reduced duty cycle and then increases the duty cycle if the bidirectional radio 206 takes over for the unidirectional radio 204 in transmitting physiological data. In one embodiment, the bidirectional radio 206 may have a reduced duty cycle that increases energy efficiency but is not dynamically configurable.

Figure 3:
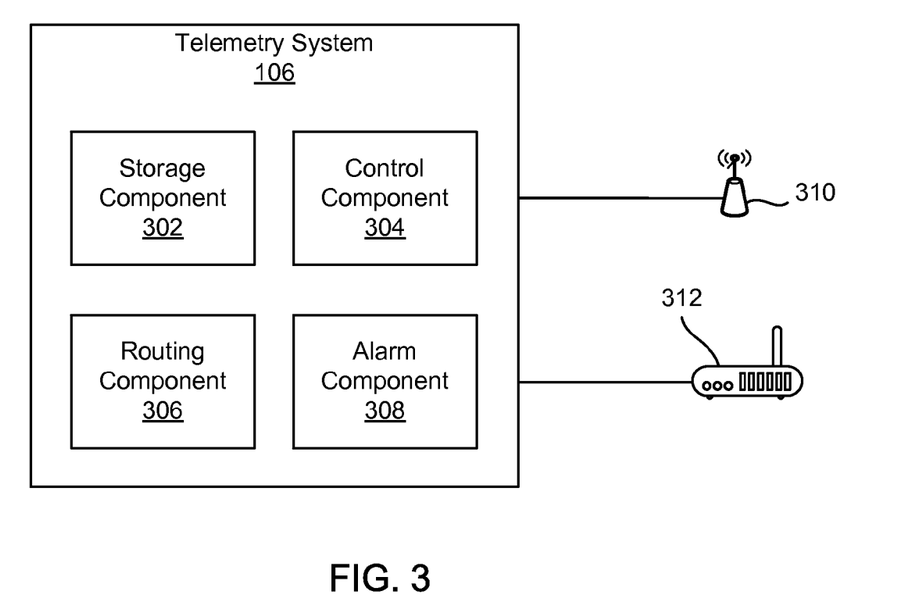
FIG. 3 is a schematic block diagram illustrating a telemetry system, according to one embodiment.

FIG. 3 is a schematic block diagram illustrating components of a telemetry system 106, according to one embodiment. The telemetry system 106 includes a storage component 302, a control component 304, a routing component 304, and an alarm component 308. The telemetry system 106 is connected to, and may include, a first radio 310 configured to operate in a first wireless frequency and a second radio 312 configured to operate in a second wireless frequency. In one embodiment, the telemetry system 106 is configured to communicate with a plurality of portable telemetry devices 102.

In one embodiment, the first radio 310 includes a receiver that is configured to operate in a same frequency band as the unidirectional radio 204 of a portable telemetry device 102. In one embodiment, the first radio 310 is configured to receive and/or transmit signals within a licensed frequency band, such as a band of the WMTS. Examples of operating frequencies include a 608 to 614 MHz range, a 1395 to 1400 MHz range, and a 1427 to 1432 MHz range.

Similarly, the second radio 312 may include a receiver and transmitter that are configured to operate in a same frequency band as the bidirectional radio 206 of a portable telemetry device 102. Using the first and second radios 310, 312, the telemetry system 106 is configured to send data to and receive data from a portable telemetry device 102, such as the portable telemetry device 102 of FIG. 2. The second radio 312 may operate within an ISM radio band such as a 2.4 to 2.5 gigahertz (GHz) range and/or a 5.725 to 5.875 GHz range. In one embodiment, the second radio 312 may include an off-the-shelf radio such as a Wi-Fi radio implementing an 802.11 standard. In one embodiment, the telemetry system 106 may communicate with a portable telemetry device 102 based on a reduced duty cycle of a bidirectional radio 206 of the portable telemetry device 102.

The storage component 302 stores physiological data received by the radios 310 and 312. When physiological data is received, the storage component 302 may identify a patient that corresponds to the data and store the physiological data in a database or location corresponding to the patient. For example, the physiological data may be transmitted with a patient identifier. The storage component 302 may look up the identifier to determine where the physiological data should be stored. In one embodiment, a plurality of different patients within a hospital or other medical center may be wearing portable telemetry devices 102. The storage component 302 may store physiological data received from each patient worn portable telemetry device 102 separately to maintain the data separately and/or securely.

The control component 304 controls the telemetry system 106 and/or one or more portable telemetry devices 102 by modifying settings and sending or receiving control data. In one embodiment, the control component 304 modifies settings by sending control data that includes alarm limit data, alarm reset data, configuration data for the portable telemetry device 102, and/or stored patient data. For example, alarm limit data may be entered by medical personnel at a patient location or other location which may then be provided to the telemetry system 106 or the portable telemetry device 102. The control component 304 may then send the alarm limit data to the portable telemetry device 102 or receive the alarm limit data from the portable telemetry device 102 to configure the alarm limit. In one embodiment, after an alarm is detected a nurse may select an option to reset an alarm. Alarm reset data may then be sent by the control component 304 to the portable telemetry device 102 to place the portable telemetry device 102 in a non-alarm state. Alternatively, if the option to reset the alarm is selected on the portable telemetry device 102, the control component 304 may receive the reset data from the portable telemetry device 102 and update information to indicate that the portable telemetry device 102 is no longer in an alarm state.

The configuration data for the portable telemetry device 102 may include data indicating which radio should be used for certain types of data communications or may indicate a remaining battery level or energy state of the portable telemetry device 102. For example, the configuration data may indicate a length of a duty cycle at which the bidirectional radio 206 should operate. Similarly, the control component 304 may send control data at a rate or interval corresponding to the duty cycle of the portable telemetry device 102. The configuration data may also include information identifying a current patient corresponding to a specific portable telemetry device 102. Upon receipt of the configuration data, the portable telemetry device 102 may update corresponding settings or information to operate in accordance with the received configuration data or other control data. In one embodiment, the control component 304 may instruct the portable telemetry device 102 to send all or a portion of patient data stored in the portable telemetry device 102 to the telemetry system 106. Transmission of stored data may be done, for example, before configuring the portable telemetry device 102 for another patient or before powering off the portable telemetry device 102. In one embodiment, the control component 304 may also provide control data that instructs the portable telemetry device 102 to send physiological data over the bidirectional radio 206.

The routing component 306 controls what type of data is sent or received using which radio. For example, the routing component 306 may determine that the telemetry system 106 and portable telemetry device 102 should operate according to a default routing configuration or a backup routing configuration. In the default routing configuration, physiological data, and/or other time-sensitive data, is communicated over a wireless frequency corresponding to the first radio 310 and the unidirectional radio 204 while control data is communicated over a wireless frequency corresponding to the second radio 312 and the bidirectional radio 206. In the backup routing configuration, all data, including physiological data and control data, is sent using the wireless frequency corresponding to the second radio 312 and the bidirectional radio 206.

In one embodiment, the routing component 306 determines which routing configuration should be used based on whether or not a unidirectional radio 204 is in range of the first radio 310 and/or whether or not a bidirectional radio 206 is in range of the second radio 312. For example, if both the unidirectional radio 204 and the bidirectional radio 206 are within range, the routing component 306 may cause the telemetry system 106 and portable telemetry device 102 to operate according to the default routing configuration. On the other hand, if the unidirectional radio 204 is out of range and the bidirectional radio 206 is within range, the routing component 306 may cause the telemetry system 106 and the portable telemetry device 102 to operate according to the backup routing configuration. The routing component 306 may dictate or set a current routing configuration by causing the control component 304 to send control data notifying the portable telemetry device 102 of the current routing configuration. In the case where the bidirectional radio 206 is out of range, the routing component 306 may not be able to change the routing setting and may allow the telemetry system 106 to continue to receive physiological data over the wireless frequency corresponding to the first radio 310 and the unidirectional radio 204, if available.

Figure 4:
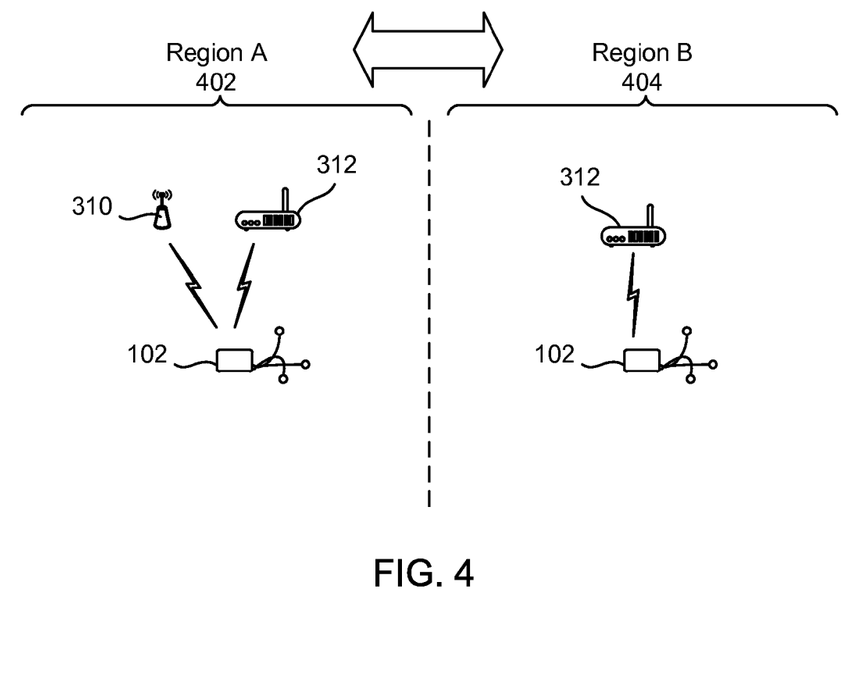
FIG. 4 is a schematic diagram illustrating a portable telemetry device in different communication environments, according to one embodiment.

FIG. 4 is a schematic diagram illustrating a portable telemetry device 102 in different communication environments, which may affect a current routing configuration for the portable telemetry device 102. Region A 402 is a region where the portable telemetry device 102 is within range of both the first radio 310 and the second radio 312. The routing component 306 may determine that both the unidirectional radio 204 and bidirectional radio 206 are within range based on the receipt of signals by the first radio 310 and the second radio 312. In this situation, the routing component 306 may set or keep the current routing setting in the default routing configuration.

Region B 404 is a region where the portable telemetry device 102 is within range of the second radio 312 but not the first radio 310. The routing component 306 may determine that the unidirectional radio 204 is out of range because the first radio 310 (or other first radios) is not receiving signals from the unidirectional radio 204 of the portable telemetry device 102. The routing component 306 may determine that the bidirectional radio 206 is within range based on the receipt of signals from the portable telemetry device 102 by the second radio 312. In this situation, the routing component 306 may set or keep the current routing setting in the default routing configuration.

The telemetry system 106 may include, or be in communication with, a plurality of first radios 310 and second radios 312. For example, a first region of a hospital may be within a coverage area of a plurality of first radios 310 used for receiving signals within a wireless frequency corresponding to unidirectional radios 204 of one or more portable telemetry devices 102. A second region of a hospital may be within a coverage area of a plurality of second radios 312 used for receiving signals within a wireless frequency corresponding to bidirectional radios 206 of the one or more portable telemetry devices 102. The first and second regions may include at least partially overlapping regions such that the one or more portable telemetry devices 102 are within range of both first and second radios 310, 312 within at least some areas of the hospital. In some embodiments, the telemetry system 106 may also be in communication with second radios 312 located within an ambulance or home of a patient. For example, a portable telemetry device 102 that is located on a patient at the patient's home may communicate with a wireless router (second radio 312) at the patient's home to send physiological and/or control data to the telemetry system 106. Similarly, a portable telemetry device 102 that is located on a patient within an ambulance or other emergency vehicle may communicate with a wireless router (second radio 312) in the vehicle to send physiological and/or control data to the telemetry system 106. In one embodiment, second radios 312 may send data to the telemetry system via one or more intervening networks such as the Internet.

Returning to FIG. 3, the alarm component 308 detects an alarm or alarm state for the portable telemetry device 102. In one embodiment, the alarm component 308 detects the alarm or alarm state by receiving an alarm signal from the portable telemetry device 102. For example, the alarm signal may be sent by the portable telemetry device 102 using the unidirectional radio 204, in which case the alarm signal would be received using the first radio 310. Alternatively, the alarm signal may be sent by the portable telemetry device 102 using the bidirectional radio 206, for example, if the current routing configuration is the backup routing configuration. In one embodiment, the alarm component 308 is configured to detect an alarm state and determine whether any received physiological data falls outside of an alarm limit or otherwise indicates an alarm state. For example, the alarm component 308 may determine whether a pulse for the patient is above an upper limit or below a lower limit. Similar determinations may be made with any type of received physiological data that is representative of the health of a patient.

Figure 5:
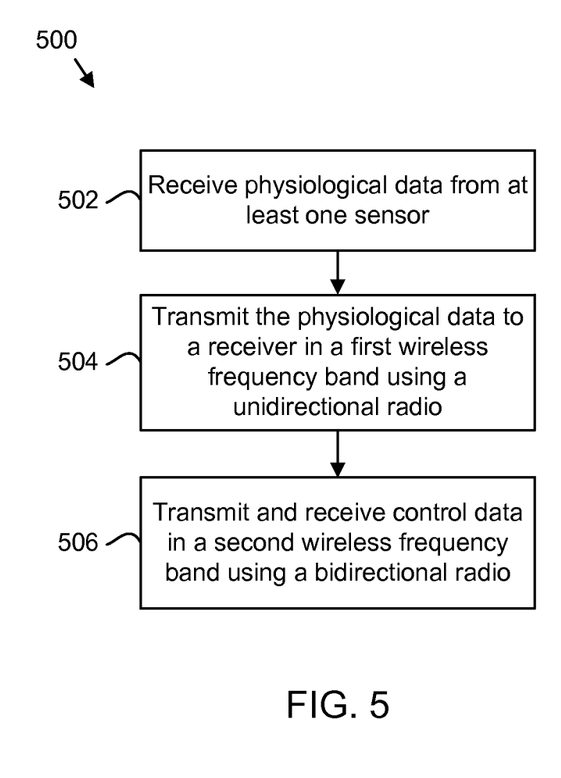
FIG. 5 is a schematic flow chart diagram illustrating a method for wireless telemetry, according to one embodiment.

FIG. 5 is a schematic flow chart diagram illustrating a method 500 for wireless telemetry, according to one embodiment. The method 500 may be performed by a portable telemetry device 102, such as a patient worn telemetry device. In one embodiment, the method 500 is performed by the portable telemetry device 102 of FIG. 2.

The method 500 begins and a measurement component 202 receives 502 physiological data from at least one sensor. The measurement component 202 may receive sensor signals over a wired connection with one or more sensors attached to a patient. For example, a portable telemetry device 102 may be worn by a patient and the one or more sensors may be attached to the patient to determine a physiological condition of the patient. The measurement component 202 may receive these signals in analog or digital form. In one embodiment, the measurement component 202 processes the signals from the sensor(s) to create processed physiological data that includes numerical and/or waveform data.

A unidirectional radio 204 transmits 504 the physiological data to a receiver in a first wireless frequency band. The physiological data may include processed or unprocessed sensor data. The unidirectional radio 204 may transmit 504 the physiological data in a licensed frequency band, such as a frequency range defined by the WMTS. The unidirectional radio 204 may transmit 504 the physiological data for receipt by a telemetry system 106 that includes a first radio 310 that is within range of the unidirectional radio 204. The unidirectional radio 204 may be directed to transmit 504 the physiological data and/or other data by a communication component 208.

A bidirectional radio 206 transmits and receives 506 control data in a second wireless frequency. The second wireless frequency may be located within an unlicensed spectrum such as an unlicensed ISM band. The bidirectional radio 206 may include an off-the-shelf radio such as an IEEE 802.11 radio. The bidirectional radio 206 may transmit and receive 506 the control data to communicate with a telemetry system 106 that includes a second radio 312 that is within range of the bidirectional radio 206. The bidirectional radio 206 may be directed to transmit and receive 506 the control data and/or other data by a communication component 208. In one embodiment, the control data configures operation of one or more of the portable telemetry device 102 and a telemetry system 106 in communication with the portable telemetry device 102.

In a further embodiment, the method 500 may also include routing all data, including physiological data or other time-sensitive data, over the bidirectional radio 206. For example, a radio backup component 210 may determine that the unidirectional radio 204 is not in range of a first radio 310 while the bidirectional radio 206 is in range of a second radio 312. In one embodiment, the radio backup component 210 may determine that the unidirectional radio 204 is not in range, or that all data should be routed over the bidirectional radio 206, based on control data sent by the telemetry system 106.

Figure 6:
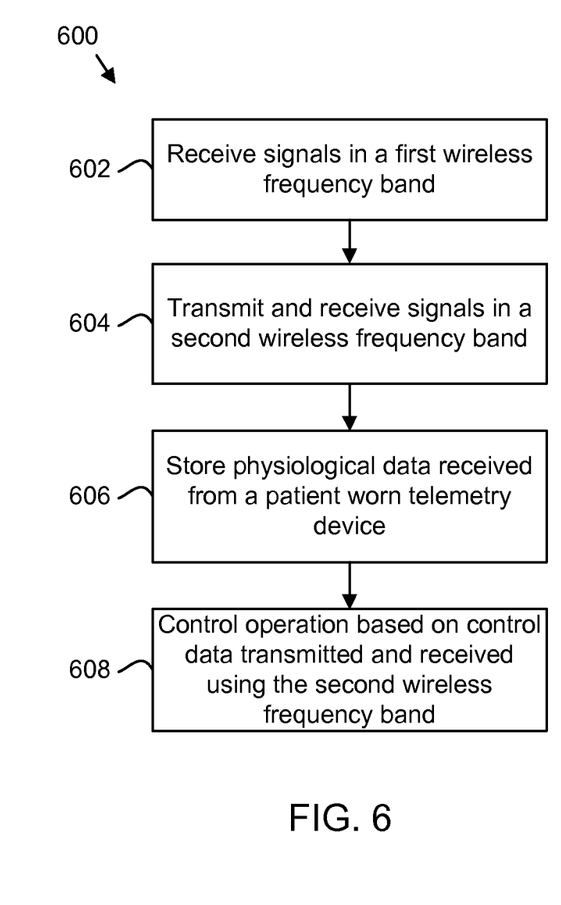
FIG. 6 is a schematic flow chart diagram illustrating a method for wireless telemetry, according to another embodiment.

FIG. 6 is a schematic flow chart diagram illustrating a method 600 for wireless telemetry, according to one embodiment. The method 600 may be performed by a telemetry system 106, such as the telemetry system of FIG. 3.

The method 600 begins and the telemetry system 106 receives 602 signals in a first wireless frequency band via a first radio 310. The first wireless frequency band may correspond to an operating frequency of a unidirectional radio 204 of a portable telemetry device 102. For example, the first wireless frequency band may include a licensed frequency band such as a band defined by the WMTS.

The telemetry system 600 transmits and receives 604 signals in a second wireless frequency band using a second radio 312. The second wireless frequency band may correspond to an operating frequency of a bidirectional radio 206 of a portable telemetry device 102. For example, the second wireless frequency band may include a licensed frequency band such as a band within an ISM band. The second radio 312 may include an off-the-shelf radio, such as an IEEE 802.11 radio.

A storage component 302 stores 606 physiological data received from a patient worn telemetry device. For example, the physiological data may be included in a signal received 602 in the first wireless frequency band by the first radio 310 when the patient worn telemetry device is in a default routing configuration. When the patient worn telemetry device is in a backup routing configuration, the physiological data may be received in the second frequency band using the second radio 312. The storage component 302 may store 606 the physiological data based on a patient identifier sent with the physiological data or an identifier of the patient worn telemetry device. For example, the storage component 302 may look up a received identifier to determine where the physiological data should be stored 606.

A control component 304 controls 608 operation of the telemetry system 106 and/or the patient worn telemetry device based on control data transmitted and received using the second wireless frequency band. For example, the control data may be included in signals transmitted and received 604 by the second radio 312. The control data may include one or more of alarm limit data, alarm reset data, configuration data for the portable telemetry device, and stored patient data. In one embodiment, the control data includes data managing a communication channel over the first wireless frequency band and/or the second wireless frequency band. For example, the control data may include scheduling for sending and/or receiving wireless messages at the telemetry system 106 or the patient worn telemetry device. In one embodiment, the control data includes data indicating a current routing configuration for the patient worn telemetry device. In one embodiment, the control component 304 may modify settings of the patient worn telemetry device by sending control data to configure or modify the settings. Similarly, the control component 304 may configure how the telemetry system 106 communicates with the patient worn telemetry device based on control data received from the portable telemetry device 102.

In a further embodiment, the method 600 may also include determining and setting a current routing configuration for the patient worn telemetry device. For example, a routing component 306 may determine whether a unidirectional radio 204 and/or a bidirectional radio 206 is within range of corresponding first or second radios 310, 312. For example, the routing component 306 may set the current routing configuration to a default routing configuration when the unidirectional radio 204 is within range of a first radio 310. Similarly, the routing component 306 may set the current routing configuration to a backup routing configuration when the unidirectional radio 204 is out of range of a first radio 310 and the bidirectional radio 206 is within range of a second radio 312. In one embodiment, the default routing configuration causes the physiological data, or other potentially time-sensitive data, to be communicated using the first wireless frequency band while control data is communicated using the second wireless frequency band. In the backup routing configuration, all data may be communicated between the telemetry system 106 and the portable telemetry device 102 using the second wireless frequency band.

Figure 7:
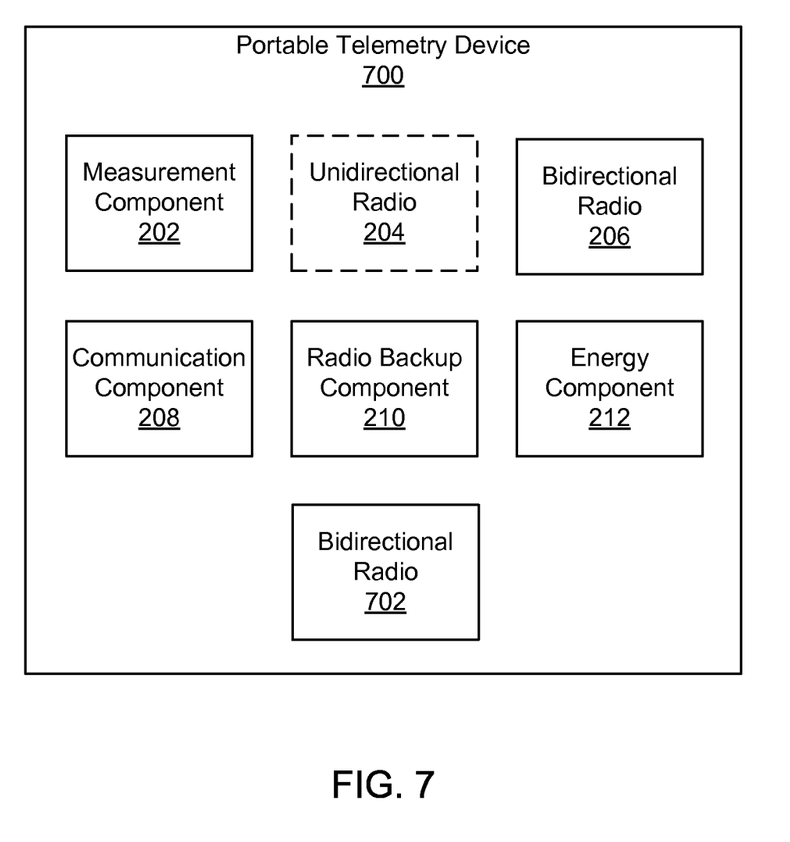
FIG. 7 is a schematic block diagram illustrating components of a portable telemetry device.

FIG. 7 is a schematic block diagram illustrating components of a portable telemetry device 700, according to another embodiment. Similar to the portable telemetry device 102 of FIG. 2, the portable telemetry device 700 includes a measurement component 202, a unidirectional radio 204, a first bidirectional radio 206, a communication component 208, a radio backup component 210, and an energy component 212. However, the portable telemetry device 700 also includes a second bidirectional radio 702, and the unidirectional radio 204 may be omitted, in some embodiments. Any of the features, functions, structures, or variations discussed in relation to components 202-212 may also be included in the portable telemetry device 700 of FIG. 7.

In one embodiment, the inclusion of two bidirectional radios may allow the portable telemetry device 700 to have more dependable coverage and/or have a larger coverage area. In one embodiment, the first bidirectional radio 206 may operate in an unlicensed spectrum such as an ISM spectrum or any other unlicensed spectrum. Thus, the first bidirectional radio 206 may include off-the-shelf parts and/or operate according to a Wi-Fi or other standard to reduce development and/or purchase costs. In one embodiment, the second bidirectional radio 702 may operate in a licensed spectrum. For example, the second bidirectional radio 702 may transmit and receive signals in a licensed spectrum corresponding to a WMTS or other specific medical service. In one embodiment, if the second bidirectional radio 702 may operate in a frequency band different from the unidirectional radio 204. For example, the second bidirectional radio 702 may operate in a licensed spectrum corresponding to a cellular network 702. This may allow the portable telemetry device 700 to provide patient data from almost any location. Thus, a patient may be able to travel to various locations while being monitored. Similarly, the portable telemetry device 700 may be used to monitor the patient as the patient is transferred between one or more of a home, hospital, ambulance, or the like. In one embodiment, first bidirectional radio 206 may be used for a licensed spectrum, such as a dedicated medical service (e.g., the WMTS) while the second bidirectional radio may be used for a different licensed spectrum, such as for communicating with a cellular network. In one embodiment, the first bidirectional radio 206 provides short-range coverage and the second bidirectional radio 702 provides a larger wide-ranging coverage area.

Various techniques, or certain aspects or portions thereof, may take the form of program code (i.e., instructions) embodied in tangible media, such as floppy diskettes, CD-ROMs, hard drives, a non-transitory computer readable storage medium, or any other machine-readable storage medium, wherein when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. The eNB (or other base station) and UE (or other mobile station) may also include a transceiver component, a counter component, a processing component, and/or a clock component or timer component. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network.

The components may be passive or active, including agents operable to perform desired functions.

Reference throughout this specification to "an example" means that a particular feature, structure, or characteristic described in connection with the example is included in at least one embodiment of the present invention. Thus, appearances of the phrase "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

It will be obvious to those having skill in the art that many changes may be made to the details of the above-described embodiments without departing from the underlying principles of the invention. The scope of the present invention should, therefore, be determined only by the following claims.

The invention claimed is:

1. A portable telemetry device comprising:
   a measurement component configured to receive, from at least one sensor, physiological data representative of a physiological condition of a patient;
   a unidirectional radio configured to transmit signals in a first wireless frequency band within a licensed wireless spectrum;
   a bidirectional radio configured to transmit and receive signals in a second wireless frequency band, wherein the second wireless frequency band does not overlap with the first wireless frequency band, and wherein the second wireless frequency band is within an unlicensed wireless spectrum; and
   a communication component configured to:
   in a default routing configuration, transmit the physiological data using the unidirectional radio and simultaneously transmit and receive control data using the bidirectional radio, wherein the control data is used for controlling operation of the portable telemetry device, and
   in a backup routing configuration, switch the physiological data between the non-overlapping frequency bands of the unidirectional radio and the bidirectional radio, such that the physiological data is transmitted using the bidirectional radio and the control data is received using the bidirectional radio,
   wherein the communication component is configured to transition from the default routing configuration to the backup routing configuration in response to a determination that the unidirectional radio is disconnected from a corresponding receiver,
   said portable telemetry device being configured as a single, portable, patient-associated, hybrid unit.

2. The portable telemetry device of claim 1, further comprising a backup component configured to route the physiological data over the bidirectional radio when the unidirectional radio is out of range and the bidirectional radio is in range.

3. The portable telemetry device of claim 1, wherein the communication component is configured to transmit time-sensitive data over the unidirectional radio, the time-sensitive data comprising one or more of the physiological data, patient identification information, and an alarm signal.

4. The portable telemetry device of claim 1, wherein the control data comprises one or more of alarm limit data, alarm reset data, configuration data for the portable telemetry device, and stored patient data.

5. The portable telemetry device of claim 1, further comprising an energy component configured to reduce a duty cycle of the bidirectional radio to reduce energy usage.

6. The portable telemetry device of claim 1, wherein the second wireless frequency band comprises a frequency band in an industrial, scientific, and medical (ISM) radio band.

7. The portable telemetry device of claim 1, wherein the first wireless frequency band is located in a licensed wireless spectrum and wherein the second wireless frequency band is located in an unlicensed wireless spectrum.

8. The portable telemetry device of claim 1, wherein the first wireless frequency band comprises a frequency band within a range defined by a wireless medical telemetry service (WMTS).

9. The portable telemetry device of claim 1, further comprising a second bidirectional radio configured to operate in a third wireless frequency band.

10. The portable telemetry device of claim 9, wherein the second wireless frequency band comprises a frequency band in an industrial, scientific, and medical (ISM) radio band and the third wireless frequency band comprises a frequency band licensed for usage by a cellular network.

11. A portable telemetry device comprising:
    a measurement component configured to receive, from at least one sensor, physiological data representative of a physiological condition of a patient;
    a unidirectional radio configured to transmit signals in a first wireless frequency band within a licensed wireless spectrum;
    a bidirectional radio configured to transmit and receive signals in a second wireless frequency band within an unlicensed wireless spectrum;
    a communication component configured to, in a default routing configuration, transmit the physiological data using the unidirectional radio and concurrently transmit and receive control data using the bidirectional radio, wherein the control data is used for controlling operation of the portable telemetry device;
    a backup component configured to, in a backup routing configuration, route the physiological data over the bidirectional radio when the unidirectional radio is out of range of a corresponding receiver and the bidirectional radio is in range of a corresponding receiver,
    wherein the communication component is configured to transition from the default routing configuration to the backup routing configuration in response to a determination that the unidirectional radio is disconnected from a corresponding receiver;
    said portable telemetry device being configured as a single, portable, patient-associated, hybrid unit.

12. A method for medical telemetry comprising:
    receiving, at a portable telemetry device, physiological data representative of a physiological condition of a patient from at least one sensor, said portable telemetry being a single, portable, patient-associated, hybrid unit;

transmitting, in a default routing configuration:
the physiological data to a receiver in a first wireless frequency band using a unidirectional radio configured to transmit data in the first wireless frequency band, and
transmitting concurrently control data in a second wireless frequency band using a bidirectional radio configured to transmit and receive signals in the second wireless frequency band;
transmitting, in a backup routing configuration, the physiological data between the non-overlapping frequency bands of the unidirectional radio and the bidirectional radio, such that the physiological data is transmitted using the bidirectional radio and the control data is received using the bidirectional radio,
wherein the second wireless frequency band does not overlap with the first wireless frequency band, and wherein the control data configures operation of one or more of the portable telemetry device and a telemetry system in communication with the portable telemetry device.

13. The method of claim 12, further comprising routing the physiological data over the bidirectional radio when the unidirectional radio is out of range of the telemetry system and the bidirectional radio is in range of the telemetry system.

14. The method of claim 12, wherein transmitting the physiological data comprises transmitting time-sensitive data over the unidirectional radio, wherein the time-sensitive data comprises one or more of the physiological data, patient identification information, and an alarm signal.

15. The method of claim 12, wherein the control data comprises one or more of alarm limit data, alarm reset data, and stored patient data.

16. The method of claim 12, further comprising reducing a duty cycle of the bidirectional radio to reduce energy usage.

17. The method of claim 12, wherein the second wireless frequency band comprises a frequency band in an industrial, scientific, and medical (ISM) radio band.

18. The method of claim 12, wherein the first wireless frequency band is located in a licensed wireless spectrum and wherein the second wireless frequency band is located in an unlicensed wireless spectrum.

19. The method of claim 12, wherein the first wireless frequency band comprises a frequency band within a range defined by a wireless medical telemetry service (WMTS).

20. A telemetry system comprising:
a first radio configured to receive signals in a first wireless frequency band;
a second radio configured to simultaneously transmit and receive signals in a second wireless frequency band, wherein the second wireless frequency band does not overlap with the first wireless frequency band;
a storage component configured to store physiological data received by the first radio from a patient worn telemetry device, the physiological data representative of a physiological condition of a patient, each said patient worn telemetry device being a single, portable, patient-associated, hybrid unit configured to transmit data selectively on either or both of the first and second wireless frequency bands; and
a control component configured to control operation of one or more of the telemetry system and the patient worn telemetry device based on control data transmitted and received using the second radio,
wherein the first wireless frequency band within a licensed wireless spectrum and the second wireless frequency band is within an unlicensed wireless spectrum; wherein at least one patient worn telemetry device comprises a communication component configured to:
in a default routing configuration, transmit physiological data using a unidirectional radio and simultaneously transmit and receive control data using a bidirectional radio, wherein the control data is used for controlling operation of the patient worn telemetry device, and
in a backup routing configuration, switch the physiological data between non-overlapping frequency bands of the unidirectional radio and the bidirectional radio, such that the physiological data is transmitted using the bidirectional radio and the control data is received using the bidirectional radio.

21. The telemetry system of claim 20, further comprising a routing component configured to provide control data to instruct the patient worn telemetry device to route the physiological data over the second wireless frequency when a unidirectional radio of the patient worn telemetry device is out of range of the first radio and a bidirectional radio of the patient worn telemetry device is within range of the second radio.

22. The telemetry system of claim 20, wherein the telemetry system is configured to receive time-sensitive data over the first radio, the time-sensitive data comprising one or more of the physiological data, patient identification information, and an alarm signal.

23. The telemetry system of claim 20, wherein the control data comprises one or more of alarm limit data, alarm reset data, configuration data for the portable telemetry device, and stored patient data.

24. The telemetry system of claim 20, wherein the second radio is configured to transmit and receive signals in the second wireless frequency based on a reduced duty cycle of a bidirectional radio of the patient worn telemetry device.

25. The telemetry system of claim 20, wherein the second wireless frequency band comprises a frequency band in an industrial, scientific, and medical (ISM) radio band.

26. The telemetry system of claim 20, wherein the first wireless frequency band is located in a licensed wireless spectrum and wherein the second wireless frequency band is located in an unlicensed wireless spectrum.

27. The telemetry system of claim 20, wherein the first wireless frequency band comprises a frequency band within a range defined by a wireless medical telemetry service (WMTS).

28. The telemetry system of claim 20, further comprising an alarm component configured to detect an alarm state based on the physiological data received from the patient worn telemetry device.

29. The telemetry system of claim 20, wherein the patient worn telemetry device comprises a first patient worn telemetry device, and wherein the storage component is configured to store physiological data received by the first radio from a plurality of patient worn telemetry devices comprising the patient worn telemetry device.

30. The telemetry system of claim 20, wherein the patient worn telemetry device comprises a first patient worn telemetry device, and wherein the control component is configured to modify settings of a plurality of patient worn telemetry devices comprising the first patient worn telemetry device based on control data transmitted and received using the second radio.

* * * * *